United States Patent [19]

Van Poucke et al.

[11] 4,032,347
[45] June 28, 1977

[54] 2-EQUIVALENT ACYLACETAMIDE YELLOW FORMING COUPLERS WITH 2,6-DIOXO-7-PURINYL COUPLING OFF GROUP

[75] Inventors: Raphael Karel Van Poucke, Berchem; Marc Willem Ailliet, Kontich; Leo August Van Wijnsberghe, 's-Gravenwezel; Gaston Jacob Benoy, Edegem, all of Belgium

[73] Assignee: AGFA-GEVAERT N.V., Mortsel, Belgium

[22] Filed: Nov. 25, 1975

[21] Appl. No.: 635,064

[30] Foreign Application Priority Data

Jan. 3, 1975 United Kingdom .................. 314/75

[52] U.S. Cl. .................................. 96/56.5; 96/100
[51] Int. Cl.² ...................... G03C 7/00; G03C 1/40
[58] Field of Search ............................ 96/100, 56.5

[56] References Cited

UNITED STATES PATENTS

| | | | |
|---|---|---|---|
| 3,933,500 | 1/1976 | Shiba et al. | 96/100 |
| 3,960,570 | 6/1976 | Oishi et al. | 96/100 |

*Primary Examiner*—David Klein
*Assistant Examiner*—Richard L. Schilling
*Attorney, Agent, or Firm*—A. W. Breiner

[57] ABSTRACT

A photographic material is described comprising novel 2-equivalent yellow forming color couplers the active methylene group of which carries a 2,6-dioxo-7-purinyl group in its oxo- or enol form.

15 Claims, No Drawings

2-EQUIVALENT ACYLACETAMIDE YELLOW FORMING COUPLERS WITH 2,6-DIOXO-7-PURINYL COUPLING OFF GROUP

The present invention relates to novel 2-equivalent colour couplers for yellow and to their use in silver halide colour elements for the production of photographic colour images.

It is known that for the production of a photographic colour image in a light-sensitive silver halide layer, the exposed silver halide is developed to a silver image by means of an aromatic primary amino compound in the presence of a colour coupler which reacts with the oxidized developing substance to form a dyestuff image corresponding to the silver image.

In the subtractive three-colour photography a light-sensitive photographic colour material is used containing red-sensitized, green-sensitized and blue-sensitive silver halide emulsion layers wherein on colour development cyan, magenta and yellow dyestuff images are formed respectively by coupling of appropriate colour couplers, with an oxidized aromatic primary amino colour developing agent.

It is common practice to use for the formation of the cyan dye image phenol or naphthol colour couplers, for the formation of the magenta dye image 2-pyrazolin-5-one colour couplers and for the formation of the yellow dye image ketomethylene couplers containing a methylene group having two carbonyl groups attached to it.

It is also known to employ besides colour couplers wherein the coupling position is unsubstituted, thus requiring for the formation of one molecule of dyestuff the development of 4 molecules of exposed silver halide, colour couplers wherein the coupling position carries a substituent that is split off upon colour development so that only two exposed silver halide molecules should be developed to form one molecule of dyestuff. The former compounds are known as 4-equivalent couplers whereas the latter are known as 2-equivalent couplers.

Prior art 2-equivalent colour couplers include yellow forming colour couplers which carry as methylene-substituents that are split off upon colour development:

1. halogen e.g. fluorine and chlorine as described e.g. in French Pat. Nos. 991,453 and 869,169, in U.S. Pat. Nos. 2,728,658 and 3,277,155 and in the published German patent application DOS No. 2,114,577;

2. the group —OR wherein R= alkyl, aryl, a heterocycle or acyl as described e.g. in British Pat. No. 1,092,506, in French Pat. Nos. 1,411,385 and 1,385,696 and in U.S. Pat. Nos. 3,447,928 and 3,408,194;

3. the group —SR as described e.g. in U.S. Pat. No. 3,265,506 and in British Pat. No. 953,454;

4. a benztriazolyl group as described in the published German patent application DOS No. 1,800,420;

5. the group —SO₃H and —SCN as described in British Pat. No. 638,039 and in U.S. Pat. No. 3,253,924;

6. the groups

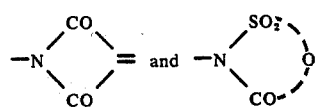

as described in the published German patent application DOS Nos. 2,163,812, 2,213,461 and 2,057,941.

The principle advantages of 2-equivalent colour couplers are known. They require approximately half as much silver halide as the 4-equivalent couplers so that in the preparation of the silver halide elements less silver halide can be used and thinner emulsion layers can be employed which results in improved resolutions and sharpness. Some groups which are split off inhibit development and couplers containing such groups are known as DIR-couplers (Development Inhibitor Releasing couplers) or ICC-couplers (Interlayer Colour Correction couplers).

From the above prior art 2-equivalent colour couplers for yellow only those with halogen as splittable group were found to be suitable in practice owing to their high coupling activity which results in high colour densities even upon rapid-processing. However, these 2-equivalent couplers still have a number of disadvantages: those containing fluorine as methylene substituent are not successful for preparative reasons and those containing chlorine as methylene substituent often impair the photographic properties of the silver halide emulsion.

As has been described in the published German patent application DOS No. 2,114,577, only particular benzoylacetanilide colour couplers with chlorine-substituted methylene group are relatively inert photographically and have little effect on colour fog formation during processing. However, these colour couplers do not satisfy all photographic requirements since photographic elements containing them still present increased fog when stored in moist and warm conditions.

In the German patent application No. 2,329,587 novel 2-equivalent colour couplers for yellow have been described. They comprise as splittable group a 5-membered nitrogen-containing unsaturated heterocyclic group linked to the active methylene group of the colour coupler through the nitrogen atom, wherein the heterocyclic group contains adjacent to said nitrogen atom, a carbon to carbon double bond, which may form part of a fused-on carbocyclic ring, e.g. a fused-on benzene ring. Imidazoles are preferred splittable groups which preferably comprise electronegative substituents e.g. nitro and alkoxycarbonyl.

The latter 2-equivalent couplers have high coupling activity and high stability during storage. However, the preparation of such heterocycles with electronegative substituents is not without problems; e.g. four reaction steps are required for the preparation of an imidazole carboxylic ester. Moreover, colour couplers with nitroimidazole splittable group, though easily accessible, are yellow coloured and therefore can give rise to colour distortions.

In accordance with the present invention novel 2-equivalent colour couplers for yellow are provided, that are easy to prepare, have high coupling activity and do not impair the photographic properties to a noteworthy extent.

The novel yellow-forming colour couplers of the present invention are ketomethylene compounds the active methylene group of which carries a 2,6-dioxo-7-purinyl group, in its oxo- or enol-form, which may carry one or more substituents.

More specifically, the 2-equivalent yellow forming colour couplers according to the present invention can be represented by the formula:

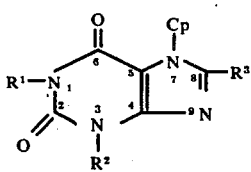

wherein:
Cp represents a yellow forming coupler residue, linked through the active methylene group, more particularly ketomethylene coupler residue e.g. an acrylacetyl coupler residue,
each of $R^1$ and $R^2$, which may be the same or different, represents hydrogen, alkyl, preferably lower alkyl, including substituted alkyl or aryl including substituted aryl, $R^1$ and $R^2$ preferably not being hydrogen simultaneously, and
$R^3$ represents hydrogen, alkyl, preferably lower alkyl, including substituted alkyl, aryl including substituted aryl, hydroxy, alkoxy, amino including substituted amino and cyclic amino e.g. cyclohexylamine and morfolino, mercapto, alkylthio, carboxy, alkoxy carbonyl and a carbamoyl group, $R^3$ preferably being hydrogen, alkyl or aryl.

Representative examples of purine compounds from which the above group in the coupling position of the yellow-forming couplers can be derived are: Xanthine (purine-2,6-dione) and the tautomeric tautoxanthine (2,6-dihydroxypurine) uric acid (purine-2,6,8-trione) and tautouric acid (2,6,8-trihydroxypurine), 1-methylxanthine, 3-methylxanthine, 1,3-dimethylxanthine (theophylline), 8-methylxanthine.

The most preferred colour couplers of the invention are those the active methylene group of which carries a 1,3-dialkyl-2,6-dioxo-7-purinyl group e.g. derived from the commercially available and relatively inexpensive theophylline (1,3-dimethyl-2,6-dioxo purine).

The yellow forming colour coupler residue Cp in the above general formula is derived from the usual known 4-equivalent colour couplers. Preferred colour coupler residues Cp are open-chain ketomethylene colour coupler residues e.g. acylacetyl coupler residues, especially acylacetamide coupler residues e.g. colour coupler residues derived from colour couplers of the type described in U.S. Pat. Nos. 3,056,675, 3,369,899, 3,393,040, 3,393,041, 3,409,439, 3,619,190, 3,645,742, 3,660,095 and 3,725,072, in Belgian Pat. No. 717,841, and in the published German patent application (DOS) Nos. 2,002,378, 2,114,576 and 2,114,578.

Preferred colour coupler residues (Cp in the above general formula) can be represented by the following general formula:

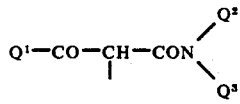

wherein:
each of $Q^1$ represents an aliphatic, aromatic or heterocyclic group and $Q^2$ represents hydrogen or a $C_1$–$C_5$ alkyl group e.g. methyl.

Representative groups for $Q^1$ are straight-chain or branched-chain alkyl group, preferably comprising from 1 to 18 C-atoms, which in the case of a secondary or tertiary alkyl group is preferably linked to the carbonyl group by means of the secondary or tertiary carbon atoms, an alkoxyalkyl group, a dicycloalkyl group, a heterocyclic or an aryl group, preferably a phenyl group which may carry one or more substituents: e.g. $C_1$–$C_{18}$ alkyl, $C_1$–$C_{18}$ alkoxy, aralkyl, aryl, aroxy, sulpho, carboxy, halogen e.g. chlorine, bromine and fluorine, hydroxy, nitro, cyano, acyl, acyloxy, acylamino, sulphoamido, amino, carbamoyl or sulphamoyl; these substituents may further be substituted by alkyl, aryl, aralkyl or a heterocycle.

Representative groups for $Q^3$ are $C_1$–$C_{18}$ alkyl, a heterocycle e.g. a 2-thiazolyl group or, preferably aryl e.g. phenyl which may be substituted by one or more substituents: e.g. $C_1$–$C_{18}$ alkyl, $C_1$–$C_{18}$ alkoxy, halogen e.g. chlorine, bromine and fluorine, hydroxy, nitro, cyano, sulpho, carboxy, aryl, aralkyl, aroxy, acyl, acyloxy, acylamino, sulphonamido, amino, carbamoyl or sulphamoyl groups which may be further substituted by alkyl, aryl, aralkyl or a heterocycle.

The 2-equivalent colour couplers according to the present invention are naturally preferably derived from corresponding 4-equivalent couplers having excellent properties as regards the absorption characteristics and stability of the dyes formed upon colour ddevelopment. Pivaloylacetanilides and benzoylacetanilides are preferred, more particularly those corresponding to the above formula wherein Cp represents one of the formulae:

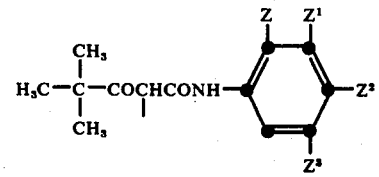

and

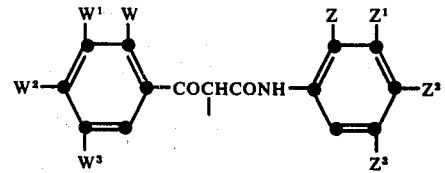

wherein:
Z represents halogen e.g. fluorine, chlorine or bromine, alkyl e.g. methyl or ethyl, alkoxy e.g. methoxy, ethoxy or hexadecyloxy, aryloxy e.g. phenoxy or methylphenoxy, or N-substituted amino e.g. N,N-dimethylamino.,
each of $Z^1$, $Z^2$ and $Z^3$, which may be the same or different, represents hydrogen, halogen e.g. fluorine, chlorine or bromine, alkyl e.g. methyl, ethyl or hexadecyl, alkoxy e.g. methoxy, ethoxy or hexadecyloxy, aryl e.g. phenyl or tolyl, arloxy e.g. phenoxy or methylphenoxy, alkoxycarbonyl e.g. methoxycarbonyl, ethoxycarbonyl or dodecyloxycarbonyl, aryloxycarbonyl, alkylsulphonyl e.g. methylsulphonyl or hexadecylsulphonyl, carbamoyl e.g. methylcarbamoyl, N-t-butylcarbamoyl, dodecylcarbamoyl, N-methyl-N-hexadecylcarbamoyl, or dimethylcarbamoyl, sulphamoyl e.g. methylsulphamoyl, dimethylsulphamoyl, N-methyl-N-hexadecylsulphamoyl, or N-(2,4-di-t-amyl phenoxy)propyl-sulphamoyl, amino or substituted amino e.g. alkylamino, arylamino and acylamino e.g. N,N- dimethylamino or N-methyl-N-hexadecylamino, anilino, acetamino, a phenoxy butyramino e.g. 2,4-di-t-amylphenoxy butyramino or ethoxycarbonylamino, an uredio group, a sulpho group or carboxyl group in acid or salt form, or a hydroxy group, and each of W, W¹, W² and W³, which may be the same or different represents hydrogen, alkyl e.g. methyl, ethyl or t-butyl, alkoxy e.g. methoxy, ethoxy or hexadecyloxy, halogen e.g. fluorine, bromine or chlorine, aryloxy e.g. phenoxy or methylphenoxy, amino and substituted amino e.g. alkylamino, aryl and acylamino. e.g. N,N-dimethylamino or N-methyl-N-hexadecylamino or an acylamino group e.g. actamino, butyramino or a phenoxybutyramino e.g. 2,4-di-t-amylphenoxybutyramino.

The novel 2-equivalent colour couplers according to the present invention can be prepared in a very simple way and with high yields by reaction of the corresponding 2-equivalent couplers having chlorine as splittable substituent on the active methylene group, with the appropriate purine heterocycle in the presence of a base as described e.g. in the German patent application No. 2,329,587. They are preferably prepared in the presence of the very strong base tetramethylguanidine, in an aprotic solvent e.g. acetonitrile or dimethylformamide as described in British patent application No. 313/75.

Apart from being easy to synthetize, the yellow forming 2-equivalent colour couplers according to the present invention have high coupling activity i.e. during colour development the heterocyclic group is easily split off which results in high colour densities. They also have high stability in the photograpic element during storage and do not increase fog as do the corresponding 2-equivalent couplers with chlorine as splittable group. Moreover, the 2-equivalent couplers of the invention yield upon colour development dyes with little side absorption in the green and red regions of the spectrum.

Representative examples of 2-equivalent colour couplers for yellow according to the present invention are listed in the following table.

Table

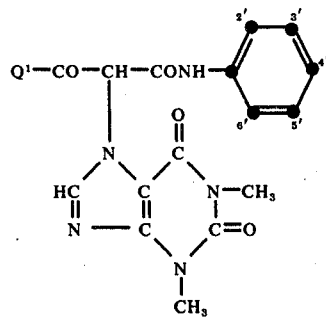

| No. | Q¹ | anilide-substituent | melting point |
|---|---|---|---|
| 1 | 4-chlorophenyl | 2'-hexadecyloxy,4'-methoxycarbonyl | 133° C |
| 2 | 4-hexadecyloxyphenyl | 2'-chloro, | 95° C |
| 3 | 2-fluorophenyl | 2'-methoxy,5'-N-methyl,N-hexadecylsulphamoyl | 65° C |
| 4 | 2-hexadecyloxyphenyl | 2'-methoxy,5'-methylsulphonyl | 132° C |
| 5 | 2-hexadecyloxyphenyl | 2'-methoxy,4'-methoxycarbonyl | 94° C |
| 6 | 2-hexadecyloxyphenyl | 2',5'-dimethoxy,4'-N,N-dimethylsulphamoyl | 120° C |
| 7 | 2-hexadecyloxyphenyl | 2'-chloro,5'-methylsulphonyl | 124° C |
| 8 | phenyl | 2'-hexadecyloxy,5'-N,N-dimethylsulphamoyl | about 50° C |
| 9 | 2-hexadecyloxyphenyl | 2'-methoxy,5'-N,N-dimethylsulphamoyl | 91° C |
| 10 | 2-hexadecyloxyphenyl | 2'-methoxy, | 67° C |
| 11 | 2,4-dimethoxyphenyl | 2'-chloro,5'-dodecyloxycarbonyl | 120° C |
| 12 | 2-chloro-4-methoxyphenyl | 2'-hexadecyloxy,5'-N,N-dimethylsulphamoyl | 79° C |
| 13 | t-butyl | 2'-hexadecyloxy,5'-N,N-dimethylsulphamoyl | 110° C |
| 14 | 4-hexadecyloxyphenyl | 2'-chloro-5'-methoxycarbonyl | 137° C |
| 15 | 4-methoxyphenyl | 2'-chloro-5'-N-methyl,N-hexadecyl sulphamoyl | 84° C |
| 16 | 4-methoxyphenyl | 2'-chloro-5'-hexadecyloxycarbonyl | 130° C |
| 17 | 4-hexadecyloxyphenyl | 2'-chloro-5'-N,N-dimethylsulphamoyl | 115° C |
| 18 | 4-methoxyphenyl | 2'-chloro-5'-N-methyl,N-hexadecyl carbamoyl | oil |
| 19 | 4-hexadecyloxyphenyl | 2',5'-dimethoxy | 114° C |
| 20 | 4-hexadecyloxyphenyl | 2'-chloro-5'-methylsulphonyl | 163° C |
| 21 | 4-hexadecyloxyphenyl | 2'-methoxy | 130° C |
| 22 | 2-hexadecyloxyphenyl | 2'-(α,α-difluoro-β-chloro-β-fluoro)-ethoxy | 75° C |

Table-continued

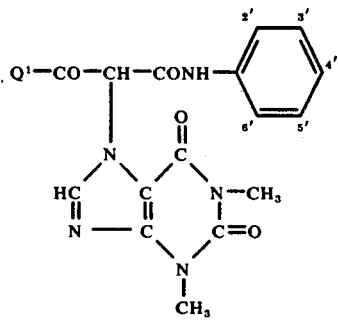

| No. | Q¹ | anilide-substituent | melting point |
|---|---|---|---|
| 23 | 4-fluorophenyl | 2'-hexadecyloxy | 83° C |
| 24 | 4-methoxyphenyl | 2'-hexadecyloxy | 101° C |
| 25 | 4-methoxyphenyl | 2',5'-dimethoxy-4'-N-methyl,N-hexadecyl sulphamoyl | 92° C |
| 26 | 4-hexadecyloxyphenyl | 2',5'-dimethoxy-4'-N,N-dimethyl sulphamoyl | 80° C |
| 27 | 4-hexadecyloxyphenyl | 2'-methoxy-5'-N-t-butyl sulphamoyl | 90° C |
| 28 | 2-hexadecyloxyphenyl | 2'-chloro-4'-methylsulphonyl | 95° C |
| 29 | 2,5-dimethoxyphenyl | 2',5'-dimethoxy-4'-N-methyl-N-hexadecyl sulphamoyl | 60° C |
| 30 | 2,4-dimethoxyphenyl | 2',5'-dimethoxy-4'-N-methyl-N-hexadecyl sulphamoyl | 104° C |
| 31 | 4-methoxyphenyl | 2',5'-dimethoxy-4'-N-methyl-N-hexadecyl sulphamoyl | 133° C |
| 32 | t-butyl | 2',5'-dimethoxy-4'-N-methyl-N-hexadecyl sulphamoyl | 104° C |
| 33 | 2,5-dimethoxyphenyl | 2'-hexadecyloxy-5'-N,N-dimethyl-sulphamoyl | 104° C |
| 34 | 2,4-dimethoxyphenyl | 2'-hexadecyloxy-5'-N,N-dimethyl-sulphamoyl | 105° C |
| 35 | 2-hexadecyloxyphenyl | 2',5'-dichloro-4'-N,N-dimethyl-sulphamoyl | 111° C |
| 36 | 4-hexadecyloxyphenyl | 2'-methoxy-5'-methoxycarbonyl | 142° C |
| 37 | 2-hexadecyloxyphenyl | 2'-methoxy-5'-carboxy | 131° C |
| 38 | 2-hexadecyloxyphenyl | 2'-methoxy-5'-methoxycarbonyl | 116° C |
| 39 | 2-hexadecyloxyphenyl | 2'-methoxy-4'-carboxy | 166° C |
| 40 | 2-hexadecyloxyphenyl | 2'-(β-ethoxy) ethoxy-5'-methyl sulphonyl | 86° C |
| 41 | t-butyl | 2'-chloro-5'-(α-2,4-di-t-amyl phenoxy)butyramido | 210° C |
| 42 | 2-hexadecyloxyphenyl | 2'-methoxy-5'-(β-methoxy) ethoxy carbonyl | 73° C |
| 43 | 2-methoxyphenyl | 2'-hexadecyloxy-5'-(β-methoxy) ethoxycarbonyl | 90° C |
| 44 | 2-methoxyphenyl | 2'-methoxy-5'-hexadecyloxycarbonyl | 128° C |
| 45 | 2-methoxyphenyl | 2'-hexadecyloxy-5'-methoxycarbonyl | 123° C |
| 46 | t-butyl | 2'-chloro-5'-methacryloylamino | 207° C |
| 47 | t-butyl | 2'-methoxy-5'-methacryloylamino | 147° C |

The above colour couplers were all prepared according to the procedure described in the following preparation:

Preparation

To a solution of 180 g (1 mole) of theophylline and 250 ml. (2 moles) of tetramethylguanidine in 3 l of acetonitrile, 680.5 g (1 mole) of α-chloro-α-(o-hexadecyloxybenzoyl)-(2',5'-dimethoxy-4'-N,N-dimethylsulphamoyl)acetanilide were added. The mixture was refluxed for 4 h, cooled and acidified by means of hydrochloric acid. The precipitate formed was filtered off by suction and washed until acid-free. The 710 g (80%) of crude product was recrystallized from 2.75 l of acetonitrile. The product was washed with methanol. Yield: 623 g (75.5%) of compound 6. Melting point: 120° C.

The yellow forming colour couplers of the present invention are particularly intended for use in photographic multicolour silver halide materials. As is known in the art, in order to obtain sufficient fastness to diffusion in hydrophilic colloid layers, more particularly a silver halide emulsion layer of the photographic element the colour couplers comprise at least one ballasting group, more particularly a straight-chain or branched-chain alkyl group having at least 5, preferably from 10 to 18 C-atoms linked directly or indirectly e.g. via —O—, —S—, —N(R)—, CON(R)—, —SO₂N(R)— wherein R is hydrogen or alkyl, —NHCO—, —NHSO₂— or another bivalent group to the groups Q¹, Q² or Q³, of the above general formula. The diffusion-fast making group can also be provided by means of an alkyl-substituted phenoxy group.

Another method of making the couplers of the invention fast to diffusion in hydrophilic colloid layers e.g. emulsion layers is to use the couplers in polymeric form e.g. by copolymerisation of acylacetanilide couplers according to the invention comprising in the benzoyl, or preferably in the anilide portion more particularly the 5-position an ethylenic group of the formula:

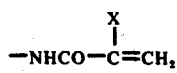

wherein X is hydrogen, halogen $C_1$-$C_5$ alkyl e.g. methyl, aralkyl or aryl, with one or more non-dye forming monomers comprising at least one ethylenic group e.g. acrylates, methacrylates, acrylic acid, methacrylic acid, acrylamides, methacrylamides, etc. The polymeric couplers are preferably prepared by emulsion polymerisation techniques e.g. as described in Belgian Pat. No. 669,971 and in United Kingdom patent No. 1,130,581.

Although the invention is particularly concerned with diffusion fast colour couplers for use in the photographic element, the yellow forming colour couplers according to the invention can also be of the diffusible type for use in developer solutions.

The present invention thus provides a method of producing photographic colour images by exposure and development with an aromatic primary amino colour developing agent of a photographic silver halide material wherein development occurs in the presence of a 2-equivalent colour coupler for yellow as defined herein.

The present invention also provides a photographic material comprising at least one silver halide emulsion layer and a 2-equivalent yellow forming colour coupler as defined herein.

In photographic colour elements, the yellow-forming colour couplers are preferably incorporated into a silver halide emulsion layer but they may also be used in a hydrophilic colloid layer in water-permeable relationship with the emulsion layer.

The colour couplers can be incorporated into hydrophilic colloid compositions according to any of the prior art methods for incorporating photographic ingredients in hydrophilic colloid media. Colour couplers comprising water-solubilizing groups e.g. carboxyl groups and sulpho groups (in acid or salt form) can be incorporated in hydrophilic colloid media from aqueous solutions. Water-insoluble or sparingly water-soluble colour couplers can be incorporated in hydrophilic colloid media from solutions in water-miscible or water-immiscible, high-boiling or low-boiling organic solvents or mixtures thereof preferably in the presence of one or more surface active agents. After having dispersed the solutions in the hydrophilic colloid medium, the low-boiling water-immiscible solvents are removed. The hydrophilic colloid medium into which the colour couplers are dispersed or dissolved need not necessarily be the coating composition of the specific hydrophilic colloid layer of the photographic element. They can be more aqueous solutions of hydrophilic colloids, e.g. gelatin which can be stored as such and incorporated into the coating composition of the specific layer just before coating.

The color couplers for yellow according to the present invention that do not comprise water-solubilizing groups have high solubility in water-immiscible high-boiling and low-boiling organic solvents and therefor are preferably incorporated from such solutions in hydrophilic colloid media.

For this purpose, the colour couplers are dissolved in a water-immiscible low-boiling solvent e.g. ethyl acetate, methylene chloride, diethyl carbonate, chloroform, etc. and/or in a water-immiscible high-boiling solvent e.g. di-n-butyl phthalate and tricresylphosphate and the solutions are dispersed in extremely fine droplets, preferably in the presence of one or more wetting or dispersing agents into the hydrophilic colloid medium e.g. aqueous gelatin, or into water, the low-boiling sparingly water-miscible solvent then being removed by evaporation. The stable dispersions of the colour couplers can be stored as such and then admixed whenever desired with the coating composition itself of the hydrophilic colloid layer such as a silver halide emulsion layer into which the compounds are intended to be present.

More details about particularly suitable techniques that may be employed for incorporating the colour couplers of the invention into a hydrophilic colloid layer of a photographic material can be found in U.S. Pat. Nos. 2,269,158 — 2,284,887 — 2,304,939 — 2,304,940 and 2,322,027, United Kingdom patent specification Nos. 791,219 — 1,098,594 — 1,099,414 — 1,099,415 — 1,099,416 — 1,099,417 — 1,218,190 — 1,272,561 and 1,297,347, French Pat. No. 1,555,663, Belgian Pat. No. 722,026, German Pat. No. 1,127,714, United Kingdom Pat. No. 1,297,947, and United Kingdom patent application No. 13,784/75.

The couplers according to the invention may be used in conjunction with various kinds of photographic emulsions. Various silver salts may be used as the sensitive salt such as silver bromide, silver iodide, silver chloride or mixed silver halides such silver chlorobromide, silver chloroiodide, silver bromoiodide and silver chlorobromoiodide. The couplers can be used in emulsions of the mixed packet type as described in United States Patent Specification 2,698,794 or emulsions of the mixed grain type as described in U.S. Pat. No. 2,592,243. The colour couplers can be used with emulsions wherein latent images are formed predominantly on the surface of the silver halide crystal, or with emulsions wherein latent images are formed predominantly inside the silver halide crystal.

The hydrophilic colloid used as the vehicle for the silver halide may be, for example, gelatin, colloidal albumin, zein, casein, a cellulose derivative, a synthetic hydrophilic colloid such as polyvinylalcohol, poly-N-vinyl pyrrolidone, etc. If desired, compatible mixtures of two or more of these colloids may be employed for dispersing the silver halide.

The light-sensitive silver halide emulsions of use in the preparation of a photographic material according to the present invention may be chemically as well as optically sensitized. They may be chemically sensitized by effecting the ripening in the presence of small amounts of sulphur containing compounds such as allyl thiocyanate, allyl thiourea, sodium thiosulphate, etc. The emulsions may also be sensitized by means of reductors for instance tin compounds as described in French Pat. No. 1,146,955 and in Belgian Pat. No. 568,687, imino-amino methane sulphinic acid compounds as described in United Kingdom patent specification No. 789,823 and small amounts of noble metal compounds such as gold, platinum, palladium, iridium, ruthenium and rhodium compounds. Chemical sensitization by means of noble metal compounds has been described by R. Koslowsky, Z. Wiss.Phot., Vol. 46, 65–72 (1951).

The said emulsions may also comprise compounds which sensitize the emulsions by development acceleration for example compounds of the polyoxyalkylene type such as alkylene oxide condensation products as described among others in U.S. Pat. Nos. 2,531,832 — 2,533,990 — 3,210,191 and 3,158,484, in United Kingdom patent specification Nos. 920,637 and 991,608 and in Belgian Pat. No. 648,710 onium derivatives of amino-N-oxides as described in United Kingdom patent specification No. 1,121,696, compounds of the type described in U.S. Pat. Nos. 3,523,796, 3,523,797, 3,552,968, 3,764,545 and 3,749,574, thioether compounds as described in British patent application Nos. 56630/72, 2865/75, 2866/75 and 2867/75, in U.S. Pat. Nos. 3,046,129 — 3,046,132 — 3,046,133 — 3,046,134 — 3,046,135 and 3,201,242, in British patent Nos. 931,018 and 1,249,248 and in French Pat. Nos. 1,218,263 and 1,351,410.

Further, the emulsions may comprise antifoggants, stabilizers e.g. heterocyclic nitrogen-containing thioxo compounds such as benzothiazoline-2-thione and 1-phenyl-2-tetrazoline-5-thione and compounds of the hydroxytriazolopyrimidine type (cfr. Birr. Z. Wiss.Phot., Vol. 47, 2–58 (1952)). They can also be stabilized with mercury compounds such as the mercury compounds described in Belgian Pat. Nos. 524,121 — 677,337 and 707,386 and in U.S. Pat. No. 3,179,520. Other suitable antifoggants for use in colour emulsions comprising the colour couplers of the invention are the aromatic disulphides as described in British Pat. No. 1,328,806 and the nitrobenzene compounds of the type described in Belgian Pat. No. 788,687.

The light-sensitive emulsion layers and adjacent layers may comprise all other kinds of ingredients such as plasticizers, hardening agents, wetting agents, etc. Examples of suitable hardening agents are formaldehyde, halogen-substituted aldehydes containing a carboxyl group e.g. mucobromic and mucochloric acid, diketones, dialdehydes, methane sulphonic acid esters, halogen-substituted triazines e.g. 2,4-dichloro-6-hydroxy-s-triazine, carbodiimides as described in U.S. Pat. Nos. 2,938,892 and 3,098,693, dihydroquinolines as described in DT-OS No. 2,332,317, carbamoylpyrimidiniums as described in DT-OS No. 2,225,230 and 2,317,677 and carbamoyloxypyridimidiniums as described in DT-OS No. 2,408,814.

The non-diffusing yellow colour formers described in the present invention are usually incorporated into a blue-sensitive silver halide emulsion for forming one of the differently sensitized silver halide emulsion layers of a photographic multilayer colour material which include positive, negative and reversal material. Such photographic multilayer colour material usually comprises a support, a red-sensitized silver halide emulsion layer with a cyan colour former, a green-sensitized silver halide emulsion layer with a magenta colour former and a blue-sensitive silver halide emulsion layer with a yellow colour former. These colour materials may further comprise one or more intermediate layers, filter layers and protective surface layers. The multilayer photographic element may comprise for the formation of each of the three colour separation images more than one e.g. two silver halide emulsion layers of different sensitivity e.g. the undermost silver halide emulsion layer being of lower sensitivity. These layers may comprise colour couplers of different coupling activity for the formation of the same colour separation image as described in DT-OS No. 1,958,709. The photographic element may comprise one or more competing couplers to improve colour reproduction by colourless coupling with oxidized developer in areas where these oxidation products should be rendered ineffective. Suitable competing couplers have been described in British Pat. Nos. 861,138 and 914,145 and in the published German Pat. Nos. 1,909,067 and 2,304,319. They may be present in silver halide emulsion layers or in intermediate and surface coatings. Emulsion layers with colour couplers of the invention and competing couplers were found to give less rise to fog formation. The photographic elements containing the yellow forming colour couplers of the present invention may comprise in the same or adjacent emulsion layer other yellow forming 2-equivalent or 4-equivalent yellow forming couplers. The elements may further comprise in addition to 2-equivalent and/or 4-equivalent magenta and cyan forming couplers masking compounds e.g. couplers containing at the coupling position phenylazo groups which are split off upon colour development as well as known DIR-couplers which upon colour development split off development-inhibiting compounds (e.g. as described in U.S. Pat. Nos. 3,227,551 and 3,632,345). They may also comprise in the layer containing the yellow forming couplers of the invention or in adjacent layers DIR-compounds which do not form dyes e.g. hydroquinone derivatives as described in U.S. Pat. Nos. 3,379,529, 3,620,746, 3,632,345 and 3,639,417 and other DIR-compounds e.g. of the type described in DT-OS No. 2,502,892.

The emulsions comprising the colour couplers of the invention are usually not sensitized spectrally. Their inherent sensitivity for the blue region of the spectrum is usually sufficient. However, it is possible to spectrally sensitize the emulsions for the blue region of the spectrum e.g. by means of sensitizing dyes as described in British Pat. Nos. 1,285,078 and 1,293,543.

The emulsions can be coated on a wide variety of photographic emulsion supports. Typical supports include cellulose ester films, polyvinylacetal film, polystyrene film, polyethylene terephthalate film and related films or resinous materials, as well as paper and glass. It is also possible to employ paper coated with α-olefin polymers e.g. paper coated with polyethylene, polypropylene, ethylene-butylene copolymers, etc.

For the production of photographic colour images according to the present invention an exposed silver halide emulsion layer is developed with an aromatic primary amino developing substance in the presence of a colour coupler according to the present invention. All colour developing agents capable of forming azomethine dyes can be utilised as developers. Suitable developing agents are aromatic compounds such as p-phenylene diamine and derivatives for example N,N-diethyl-p-phenylene diamine, N-butyl-N-sulphobutyl-p-phenylene diamine, 4-amino-3-methyl-N-ethyl-N-(β-hydroxyethyl)aniline sulphate, 2-amino-5-diethylamino-toluene, 4-amino-N-ethyl-N(β-methanesulphonamidoethyl)-m-toluidine, N-hydroxyethyl-N-ethyl-p-phenyle diamine, etc.

The developing compositions may comprise the usual ingredients as well as development activating compounds including polyoxyethylene compounds, onium compounds and organic thioethers as referred to hereinbefore, antifoggants e.g. nitrobenzene compounds of the type described in the Belgian Pat. No. 788,687, etc.

The following examples illustrate the present invention.

EXAMPLE 1

A gelatino silver chlorobromoiodide emulsion (0.6 mole % of iodide, 28 mole % of chloride) comprising per kg 96 g of gelatin and an amount of silver halide equivalent to 106.6 g of silver nitrate was divided into 3 emulsion portions A, B and C. To each emulsion portion one of the following colour couplers were added in an amount of 0.542 mole per mole of silver halide from a dispersion in gelatin:

emulsion A : α-chloro-α-(2-hexadecyloxybenzoyl)-(2'-methoxy-5'-methylsulphonyl)acetanilide
emulsion B : colour coupler No. 6 of the above table.
emulsion C : colour coupler No. 5 of the above table.

The coupler dispersions in gelatin were prepared as follows : 1 g of colour coupler was dissolved in 3 ml of ethyl acetate at 45° C and the coupler solution was dispersed into a 5% aqueous gelatinous solution containing an anionic surfactant. The solvent was removed by evaporation whereupon the coupler dispersion in gelatin was added to the photographic emulsion.

After addition of the common additives such as stabilizers, wetting agents, spectral sensitizers and hardeners, the emulsions were coated pro rata of 80 g per sq.m. to form part of a multilayer three-colour photographic film element comprising in addition to the blue-sensitive emulsion layer with colour coupler for yellow, a red-sensitized emulsion layer containing a colour coupler for cyan and a green-sensitized emulsion layer containing a colour coupler for magenta.

After drying, strips of the materials A, B and C formed were exposed for 1/20 s through a continuous wedge and developed for 10 min at 24° C in a developing bath of the following composition:

| | |
|---|---|
| sodium hexametaphosphate | 2 g |
| anhydrous sodium sulphite | 4 g |
| anhydrous sodium carbonate | 17 g |
| potassium bromide | 2 g |
| 2-amino-5-diethylaminotoluene hydrochloride | 3 g |
| water to make | 1 liter |
| | (pH 10.65) |

The developed materials were treated for 5 min. at 24° C in a fixing bath of the following composition:

| | |
|---|---|
| water | 600 ml |
| sodium thiosulfate-5-water | 240 g |
| sodium sulphite | 15 g |
| glacial acetic acid | 13.4 ml |
| anhydrous boric acid | 7.5 g |
| potassium alum-12-water | 15 g |
| water to make | 1 liter |
| | (pH 4.25) |

The materials were rinsed for 2 minutes with water and then bleached for 8 minutes at 24° C in a bleach bath of the following composition:

| | |
|---|---|
| water | 800 ml |
| anhydrous potassium bromide | 20 g |
| anhydrous potassium dichromate | 5 g |
| potassium alum-12-water | 40 g |
| water to make | 1 liter |
| | (pH 3.1) |

After bleaching, the materials were rinsed with water for 5 min and fixed for 5 min at 24° C in the above mentioned fixing solution.

After a final rinsing for 8 min the materials were dried. Grey wedge images were obtained (by using the appropriate colour filters during exposure) and the sensitometric results measured behind a blue filter are listed in the following table I:

Table I

| Element | Fog | Relative speed | Gradation |
|---|---|---|---|
| A | 0.11 | 100 | 3.66 |
| B | 0.09 | 71 | 2.80 |
| C | 0.09 | 87 | 4.10 |

Other strips of the photographic elements A, B, C were exposed and processed as described hereinbefore with the difference that the elements were developed in the above mentioned developer for 16 min instead of 10 min before and after having been stored for a week at a temperature of 57° C and a relative humidity of 34%.

The results are given in table II.

Table II

| | Fog | | Relative speed | |
|---|---|---|---|---|
| Element | before storing | after storing | before storing | after storing |
| A | 0.20 | 0.27 | 100 | 105 |
| B | 0.17 | 0.18 | 83 | 77 |
| C | 0.13 | 0.17 | 83 | 86 |

As compared with the photographic material comprising a 2-equivalent coupler carrying chlorine as substituent on the methylene group, the photographic elements of the invention comprising the colour couplers described hereinbefore show less fog even after storing for only a small loss in sensitivity. The speed is expressed on a percentage basis.

EXAMPLE 2

Example 1 was repeated with the only difference that the three emulsions A, B and C now also comprised 0.037 mole of the competing coupler : 1-p-sulphophenyl-3-heptadecyl-4-methyl-2-pyrazolin-5-one.

After coating, exposure and processing as described in example 1 grey wedge images were obtained. The results are listed in table III (10 min development) and table IV (16 min development + storing).

Table III

| Element | Fog | Relative speed | Gradation |
|---|---|---|---|
| A | 0.12 | 100 | 3.50 |
| B | 0.09 | 79 | 2.70 |
| C | 0.09 | 79 | 3.30 |

Table IV

| | Fog | | Relative speed | |
|---|---|---|---|---|
| Element | before storing | after storing | before storing | after storing |
| A | 0.23 | 0.48 | 100 | 75 |
| B | 0.12 | 0.16 | 86 | 89 |
| C | 0.12 | 0.15 | 86 | 89 |

The above results show a considerable lower fog level for elements B and C compared to element A.

EXAMPLE 3

Example 2 was repeated with the only difference that 1-(p-methylsulphonylphenyl)-3-[β-(2-tetradecyl-4-chloro-5-methylphenoxy)-ethoxycarbonylamino]-4-methyl-2-pyrazolin-5-one was used as competing coupler.

The results are listed in table V (10 min development) and table VI (16 min development + storing).

Table V

| Element | Fog | Relative speed | Gradation |
| --- | --- | --- | --- |
| A | 0.11 | 100 | 3.60 |
| B | 0.08 | 89 | 3.10 |
| C | 0.08 | 77 | 3.90 |

Table VI

| Element | Fog before storing | Fog after storing | Relative speed before storing | Relative speed after storing |
| --- | --- | --- | --- | --- |
| A | 0.21 | 0.32 | 100 | 115 |
| B | 0.14 | 0.15 | 87 | 79 |
| C | 0.13 | 0.16 | 87 | 91 |

The improved sensitometric qualities of elements B and C as compared with those of element A are obvious.

EXAMPLE 4

A gelatino silver bromoiodide emulsion (3.7% of iodide), comprising per kg 90 g of gelatin and an amount of silver halide equivalent to 70 g of silver nitrate was divided into 3 emulsion portions A, B and C.

To each of the portions one of the following colour couplers were added from gelatin dispersions prepared as described in example 1:

emulsion A : 0.08 mole of α-chloro-α-(2-hexadecyloxybenzoyl)-(2'-methoxy-5'-methylsulphonyl) acetanilide and 0.0363 mole of α-benzoyl-(2'-hexadecyloxy-5-N,N-dimethylsulphamoyl) acetanilide per mole of silver halide
emulsion B : 0.114 mole of colour coupler No. 6.
emulsion C : 0.114 mole of colour coupler No. 5.

To each emulsion an amount of 0.028 mole of the competing coupler : 1-p-sulphophenyl-3-heptadecyl-4-methyl-2-pyrazolin-5-one was added per mole of silver halide.

After addition of the common additives such as spectral sensitizers, stabilizers, wetting agents and hardeners, the emulsions were coated pro rata of 83 g per sq.m on a film support.

The emulsion layers were dried and overcoated with a gelatin antistress layer. After drying, strips of the materials A, B and C formed were exposed for 1/20 s through a continuous wedge and developed following a common reversal processing sequence. After initial rinsing, the coated layers were developed in a black-and-white developer (3 min at 25° C) of the following composition :

| | | |
| --- | --- | --- |
| sodium hexametaphosphate | 2 | g |
| anhydrous sodium sulphite | 50 | g |
| hydroquinone | 6 | g |
| 1-phenyl-3-pyrazolidinone | 0.5 | g |
| anhydrous sodium carbonate | 25 | g |
| potassium bromide | 2.3 | g |
| potassium thiocyanate | 3 | g |
| potassium iodide | 6 | mg |
| water to make | 1 | liter |
| | (pH 10.2) | |

After stopping the black-and-white development and washing, the coated layers were re-exposed and then redeveloped in a colour developer (4 min 30 s) with the following composition :

| | | |
| --- | --- | --- |
| sodium hexametaphosphate | 2 | g |
| anhydrous sodium sulphite | 4 | g |
| N,N-diethyl-p-phenylenediamine hydrochloride | 2.7 | g |
| anhydrous sodium carbonate | 25 | g |
| potassium bromide | 0.75 | g |
| sodium hydrogen carbonate | 0.3 | g |
| potassium iodide | 4 | mg |
| water to make | 1 | liter |
| | (pH 10.7) | |

The thus developed materials were treated for 30 s at 25° C in a fixing bath, then washed for 1 min then bleached for 2 min at 25° C in a bleaching bath and then fixed again for 1 min at 25° C in the fixing bath. After final rinsing, the materials were dried. The fixing bath had the following composition :

| | | |
| --- | --- | --- |
| anhydrous sodium sulphite | 10 | g |
| sodium metabisulphite | 8.75 | g |
| boric acid | 6.25 | g |
| sodium acetate | 17.5 | g |
| glacial acetic acid | 14.3 | ml |
| aluminium chloride | 10 | g |
| ammonium thiosulfate | 17.5 | g |
| water to make | 1 | liter |
| | (pH 4.3) | |
| The bleach bath had the following composition: | | |
| potassium hexacyanoferrate(III) | 40 | g |
| potassium bromide | 30 | g |
| sodium acetate-3-water | 5 | g |
| glacial acetic acid | 5 | ml |
| sodium hydrogen sulphate | 11 | g |
| sodium salt of ethylenediamine tetraacetic acid | 10 | g |
| water to make | 1 | liter |
| | (pH 4.1) | |

Yellow coloured wedge reversal images were obtained. The sensitometric results of the above processed strips and of strips which were exposed and processed after having been stored for 3 days at 57° C and 34% relative humidity or at 35° C and 80% relative humidity are listed in the following table VII.

Table VII

| Material | Minimum density without storing | Minimum density after storing at 57° C/ 34 % RH | Minimum density after storing at 35° C/ 80 % RH | Relative speed before storing | Relative speed after storing at 57° C/ 34 % RH | Relative speed after storing at 35° C/ 80 % RH | Maximum density before storing | Maximum density after storing at 57° C/ 34 % RH | Maximum density after storing at 35° C/ 80 % RH |
| --- | --- | --- | --- | --- | --- | --- | --- | --- | --- |
| A | 0.07 | 0.07 | 0.09 | 100 | 28 | 49 | 1.08 | 1.00 | 1.20 |
| B | 0.05 | 0.05 | 0.05 | 86 | 63 | 45 | 1.61 | 1.56 | 1.91 |

Table VII-continued

| Material | Minimum density | | | Relative speed | | | Maximum density | | |
|---|---|---|---|---|---|---|---|---|---|
| | without storing | after storing at 57° C/ 34 % RH | after storing at 35° C/ 80 % RH | before storing | after storing at 57° C/ 34 % RH | after storing at 35° C/ 80 % RH | before storing | after storing at 57° C/ 34 % RH | after storing at 35° C/ 80 % RH |
| C | 0.05 | 0.04 | 0.05 | 98 | 72 | 49 | 1.50 | 1.37 | 1.75 |

The above results prove the superior properties of elements B and C comprising colour couplers of the invention.

EXAMPLE 5

Strips of the elements described in example 4 were exposed and processed as described in example 1 with the difference, however, that the colour development occurred in the developer of example 4 for 3 min at 25° C and that the materials were fixed and bleached as described in example 4.

The results are listed in table VIII.

Table VIII

| Material | Fog | Relative speed | Gradation |
|---|---|---|---|
| A | 0.48 | 100 | 0.6 |
| B | 0.07 | 91 | 0.8 |
| C | 0.06 | 83 | 0.8 |

EXAMPLE 6

The colour couplers listed in the following table were incorporated into a conventional silver iodobromide (2.3 mole % of iodide) emulsion in an amount of about 0.006 mmole of coupler per mole of silver halide.

The couplers were incorporated from aqueous gelatin dispersions obtained by dissolving the couplers in ethyl acetate, dispersing the solution in aqueous gelatin and removing the ethylacetate by evaporation under reduced pressure.

The emulsion portions were coated on a conventional film support, dried and overcoated with a gelatin antistress layer. After having been dried, the emulsions were exposed through a step-wedge and developed in conventional colour developer baths, containing as developing agents the compounds listed in the following table, to form negative silver images and magenta dye images.

The silver images and residual silver halide were removed by treatment with a conventional bleach and a sodium thiosulphate fixer.

The yellow dye images had maximum densities as listed in the table below. The colour developing agents listed in the table are :

$CD_2$ = 2-amino-5-diethylamino-toluene hydrochloride
$CD_3$ = 2-amino-5-[N-ethyl-N-($\beta$-methylsulphonylamino)ethyl] aminotoluene sulphate
$CD_4$ = 4-amino-3-methyl-N-ethyl-N-($\beta$-hydroxyethyl)aniline sulphate.

| Coupler | Colour developing agent | $D_{max}$ |
|---|---|---|
| 2 | $CD_2$ | 2.46 |
| | $CD_3$ | 2.40 |
| | $CD_4$ | 1.99 |
| 4 | $CD_2$ | 2.24 |
| | $CD_3$ | 2.05 |
| 13 | $CD_2$ | 1.95 |
| | $CD_3$ | 1.95 |
| | $CD_4$ | 1.92 |
| 27 | $CD_2$ | 2.48 |
| | $CD_3$ | 2.58 |
| | $CD_4$ | 2.18 |
| 34 | $CD_2$ | 2.04 |

-continued

| Coupler | Colour developing agent | $D_{max}$ |
|---|---|---|
| | $CD_3$ | 1.80 |
| | $CD_4$ | 1.93 |
| 32 | $CD_2$ | 2.51 |
| | $CD_3$ | 2.42 |
| | $CD_4$ | 2.24 |
| 30 | $CD_2$ | 2.02 |
| | $CD_3$ | 1.94 |
| 29 | $CD_2$ | 2.03 |
| | $CD_3$ | 1.84 |

We claim:

1. A photographic material comprising at least one silver halide emulsion layer and a 2-equivalent yellow forming ketomethylene colour coupler wherein the active methylene group carries a 2,6-dioxo-7-purinyl group in its oxo- or enol form and has the formula:

$$R^1-N\begin{array}{c}O\\ \end{array}\begin{array}{c}Cp\\N\\ \\C-R^3\\ \|\\N\end{array}$$
$$O=\begin{array}{c}\\N\\|\\R^2\end{array}$$

wherein:
Cp represents a yellow forming open-chain acylacetamide coupler residue linked through the active methylene group,
each of $R^1$ and $R^2$, which may be the same or different, represents hydrogen, an alkyl group, or an aryl group, and
$R^3$ represents hydrogen, an alkyl group, an aryl group, a hydroxy group, an alkoxy group, an amino group, a mercapto group, an alkylthio group, a carboxy group, an alkoxycarbonyl group or a carbamoyl group.

2. A photographic material according to claim 1, wherein $R^1$ and $R^2$ are alkyl.

3. A photographic material according to claim 2, wherein $R^1$ and $R^2$ are methyl.

4. A photographic material according to claim 1, wherein the yellow forming colour coupler residue carrying the heterocyclic substituent at the coupling position corresponds to the formula :

$$Q^1-CO-CH-CON\begin{array}{c}Q^2\\ \diagup\\ \diagdown\\Q^3\end{array}$$

wherein :
each of $Q^1$ and $Q^3$, which may be the same or different, represents an aliphatic, aromatic or heterocyclic group, and
$Q^2$ represents hydrogen or $C_1-C_5$ alkyl.

5. A photographic material according to claim 4, wherein

Q¹ represents an alkyl group, an alkoxyalkyl group, a dicycloalkyl group, a heterocycle or an aryl group, Q² represents hydrogen or $C_1$–$C_5$ alkyl, and Q³ represents $C_1$–$C_{18}$ alkyl, a heterocycle or an aryl group.

6. A photographic material according to claim 5, wherein the yellow forming colour coupler is a pivaloyl acetanilide colour coupler or a benzoylacetanilide colour coupler.

7. A photographic material according to claim 6, wherein R¹ and R² are alkyl.

8. A photographic material according to claim 7, wherein R¹ and R² are methyl.

9. A photographic material according to claim 8, wherein the yellow forming colour coupler residue corresponds to one of the formulae:

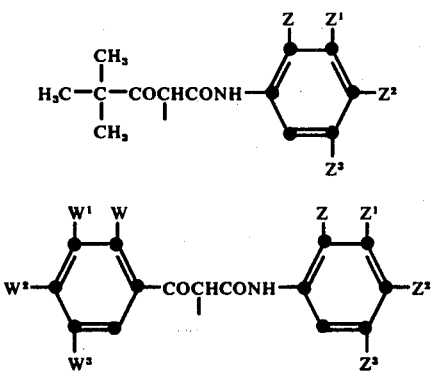

wherein:

Z represents a halogen atom or an alkyl, alkoxy, aryloxy or amino group, each of Z¹, Z² and Z³, which may be the same or different represents a hydrogen or halogen atom, an alkyl, alkoxy, aryl, aryloxy, alkoxycarbonyl, aryloxycarbonyl, alkylamino, arylamino, alkylsulphonyl, carbamoyl, sulphamoyl, acylamino, ureido, or hydroxy group or a sulpho or carboxy group in acid or salt form, and each of W, W¹, W² and W³, which may be the same or different represents a hydrogen or halogen atom or an alkyl, alkoxy, aryloxy or amino group.

10. A photographic material according to claim 1, wherein the material also comprises a competing coupler in a light-sensitive or in a non-light-sensitive hydrophilic colloid layer.

11. A photographic material according to claim 1, wherein the yellow forming colour coupler is present in a silver halide emulsion layer.

12. A photographic material according to claim 1, wherein the yellow forming colour coupler is present in a non-light-sensitive hydrophilic colloid layer.

13. Method of producing coloured photographic images in a photographic light-sensitive silver halide material which comprises exposing the material and developing it with an aromatic primary amino colour developing agent in the presence of a 2-equivalent yellow forming ketomethylene colour coupler wherein the colour coupler carries at the active methylene group a 2,6-dioxo-7-purinyl group in its oxo- or enol form and has the formula:

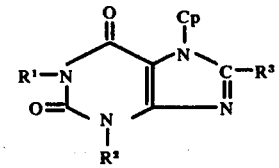

wherein:

Cp represents a yellow forming open-chain acylacetamide coupler residue linked through the active methylene group, each of R¹ and R², which may be the same or different, represents hydrogen, an alkyl group, or an aryl group, and R³ represents hydrogen, an alkyl group, an aryl group, a hydroxy group, an alkoxy group, an amino group, a mercapto group, an alkylthio group, a carboxy group, an alkoxycarbonyl group or a carbamoyl group.

14. Method according to claim 13, wherein R¹ and R² are alkyl.

15. Method according to claim 14, wherein R¹ and R² are methyl.

* * * * *